(12) United States Patent
Mertens

(10) Patent No.: US 10,717,789 B2
(45) Date of Patent: Jul. 21, 2020

(54) INULIN PRODUCT

(71) Applicant: TIENSE SUIKERRAFFINADERIJ N.V., Brussels (BE)

(72) Inventor: Linda Mertens, Schaarbeek (BE)

(73) Assignee: TIENSE SUIKERRAFFINADERIJ N.V. (BE)

( * ) Notice: Subject to any disclaimer, the term of this patent is extended or adjusted under 35 U.S.C. 154(b) by 236 days.

(21) Appl. No.: 15/747,666

(22) PCT Filed: Aug. 3, 2016

(86) PCT No.: PCT/EP2016/001336
§ 371 (c)(1),
(2) Date: Jan. 25, 2018

(87) PCT Pub. No.: WO2017/021005
PCT Pub. Date: Feb. 9, 2017

(65) Prior Publication Data
US 2018/0215838 A1    Aug. 2, 2018

(30) Foreign Application Priority Data
Aug. 5, 2015 (EP) .................................. 15002339

(51) Int. Cl.
| | |
|---|---|
| *C08B 37/00* | (2006.01) |
| *A23K 20/163* | (2016.01) |
| *A23K 50/40* | (2016.01) |
| *C08L 5/00* | (2006.01) |
| *C12P 19/04* | (2006.01) |

(52) U.S. Cl.
CPC ........ *C08B 37/0054* (2013.01); *A23K 20/163* (2016.05); *A23K 50/40* (2016.05); *C08L 5/00* (2013.01); *C12P 19/04* (2013.01)

(58) Field of Classification Search
CPC .................................................. C08B 37/0054
See application file for complete search history.

(56) References Cited

U.S. PATENT DOCUMENTS

| | | | |
|---|---|---|---|
| 2001/0016572 A1 | 8/2001 | De Leenheer et al. | ......... 514/23 |
| 2015/0079245 A1* | 3/2015 | Frooninckx | ......... C08B 37/0051 426/271 |

FOREIGN PATENT DOCUMENTS

WO    WO2009129985    10/2009 ............. C08B 37/00

OTHER PUBLICATIONS

International Search Report and Written Opinion issued in application No. PCT/EP2016/001336, dated Oct. 7, 2016 (8 pgs).
Hoebregs et al., "Determination of Oligofructose, a Soluble Dietary Fiber, by High-Temperature Capillary Gas Chromatography", Joye & Hoebregs: Journal of AOAC International, vol. 83, No. 4, 2000 pp. 1020-1026.

* cited by examiner

*Primary Examiner* — Jenna A Watts
(74) *Attorney, Agent, or Firm* — Hayes Soloway P.C.

(57) ABSTRACT

A polydisperse inulin product has a factor L, defined as a ratio S/D, wherein:
S equals the sum of the compounds $GF_2$, $F_3$, and $F_4$ in the inulin product, expressed in wt. % on total carbohydrates;
D equals $[(F_i/G_i)+1]$, wherein $F_i$ is the amount of inulin-related fructose in the inulin product, $G_i$ is the amount of inulin-related glucose in the inulin product, whereby $F_i$ and $G_i$ are expressed in wt. % on total carbohydrates, wherein the value of L lies between 2.0 and 3.0 and wherein between 3 and 20 wt. % on total carbohydrates of the inulin product is:
$GF_n$ compounds wherein n is 10 or greater, and/or
$F_m$ compounds wherein m is 11 or greater.

18 Claims, No Drawings

INULIN PRODUCT

BACKGROUND OF THE INVENTION

The invention relates to an inulin product.

A common characteristic of inulin products such as native inulin from chicory root is that the inulin products easily lead to gel formation when put into water, all the more so if this is done at higher concentrations such as at solids contents of 60%, 65%, or 70% or more. While such gel formation may be sometimes desirous, it is also frequently not wanted.

US-A-2001/016572 relates to a method for preparing a polydispersed saccharide composition poor in glucose (G), fructose (F) and saccharose (GF) containing at least 93.5% by weight per dry matter of fructo-ollgosaccharides constituted by a chain of fructose units with a terminal glucose of formula $GF_n$, n and m being between 2 and 20 and comprising a content of glucose, fructose and saccharose in total less than 5% by weight per dry matter. The method consists in subjecting a substance containing fructanes to partial hydrolysis, the said substance containing fructanes of an average degree of polymerisation not less than 7 and containing glucose, fructose and saccharose in total at most 3.5% by weight per dry matter.

WO-A-2009/129985 relates to an aqueous dispersion of fructan-containing particles, wherein the $D_{50}$ of the fructan-containing particles lies between 2 μm and 50 μm and the solids content of the aqueous dispersion as a whole lies between 61 wt. % and 80 wt. %. The invention further relates to a process for the preparation of an aqueous dispersion of fructan-containing particles, comprising: a) the step of bringing fructan and water together to form a mixture; b) optionally a hydrolysis step, wherein a portion of the fructans in the mixture is hydrolysed, such that at the end of this step b) between 5 wt. % and 25 wt. % of all fructans in the mixture are essentially non-soluble at room temperature; c) optionally a purification step, wherein the mixture is brought into contact with a purification agent, followed by removal of the purification agent from the mixture; d) a concentrating step, wherein the mixture is concentrated, such that the solids content lies between 61 and 80%, whereby the aqueous dispersion is formed.

SUMMARY OF THE INVENTION

It is the objective of the present invention to provide an inulin product that provides the typical and desirable properties associated with inulin, while having at the same time a dearly reduced tendency towards gel formation.

According to the present invention, the inulin product is polydisperse and has a factor L, defined as a ratio S/D, wherein:
  S equals the sum of the compounds $GF_2$, $F_3$, and $F_4$ in the inulin product expressed in wt. % on total carbohydrates;
  D equals $[(F_i/G_i)+1]$, wherein $F_i$ is the amount of inulin-related fructose in the inulin product, $G_i$ is the amount of inulin-related glucose in the inulin product, whereby $F_i$ and $G_i$ are expressed in wt. % on total carbohydrates,
wherein the value of L lies between 2.0 and 3.0, and wherein between 3 and 20 wt. % on total carbohydrates of the inulin product consists of:
  $GF_n$ compounds wherein n is 10 or greater, and/or
  $F_m$ compounds wherein m is 11 or greater.

It is an advantage of the inulin product of the invention that any tendency to gel formation in aqueous dispersions is greatly reduced or even absent.

The invention relates to an inulin product. Inulin as such is known, and has herein common meaning of being a—usually polydisperse—carbohydrate oligomer or polymer consisting mainly of fructosyl-fructose links with optionally a glucose starting unit. The fructosyl-fructose links in inulin are mainly of the $\beta(2\rightarrow 1)$ type.

As used herein, the meaning of the term inulin encompasses as such also the compounds known as oligofructose; typical of oligofructoses is that they are inulin compounds whereby the degree of polymerisation (DP) ranges from 2 to 10. In practice, oligofructose is also referred to as fructooligosaccharide; as meant herein, these terms are considered to be synonyms.

Glucose units are herein referred to as 'G', and fructose units are herein referred to as 'F'. Thus, sucrose can be represented as 'GF', and an individual inulin compound can be represented as '$GF_n$' or as '$F_m$' whereby n and m are integers having a value of 2 or higher.

The inulin product according to the invention is polydisperse. The term polydisperse as used herein has the meaning of indicating that the product concerned consists of a mixture of compounds of different degrees of polymerisation.

One important characteristic of the inulin product of the invention is the sum of the compounds $GF_2$, $F_3$, and $F_4$, expressed in wt. % on total carbohydrates of the inulin product; this sum should be determined separately and is herein designated as factor 'S'. One suitable known method of determining the amounts of the compounds $GF_2$, $F_3$, and $F_4$ is via high-temperature capillary gas chromatography (HGC) using the specific method as disclosed in: Joye & Hoebregs, J. AOAC International, Vol. 83, No. 4, 2000, pp 1020-1025.

A further important characteristic of the inulin product of the invention is the total amount of inulin-related fructose $F_i$, being the wt. % (as percentage of total carbohydrates) of fructose in the inulin product which is bound in the form of $GF_n$ or $F_m$. Thus, any free fructose and any fructose bound in sucrose or in other non-inulin compounds does not contribute to $F_i$. One suitable known way of determining $F_i$ is via method AOAC 997.08 (version 2013). The said method involves a full enzymatic hydrolysis of the inulin product, leading to a mixture wherein all F and G units which were bound in $GF_n$ or $F_m$ or in other carbohydrates are turned into free fructose and free glucose. The amount of free fructose is then determined via a suitable analytical method such as HGC. The result must then be corrected for fructose from non-inulin origin; thus, the amount of free fructose in the original sample (prior to hydrolysis) and the amount fructose-containing non-inulin products such as for example sucrose in the original sample (prior to hydrolysis) should be determined as well; HGC is a suitable method here too.

Yet another important characteristic of the inulin product of the invention is the total amount of inulin-related glucose $G_i$, being the wt. % (as percentage of total carbohydrates) of glucose in the inulin product which is bound in the form of $GF_n$. Thus, any free glucose and any glucose bound in sucrose or in non-inulin compounds does not contribute to $G_i$. One suitable known way of determining $G_i$ is via method AOAC 997.08 (version 2013), i.e. the same method as is suitable for determining $F_i$. In fact, $G_i$ and $F_i$ of an inulin product can be—and often are—determined simultaneously.

According to the invention, $F_i$ and $G_i$ are used to calculate a factor 'D', which is defined as: $D=[(F_i/G_i)+1]$.

The determination of factors S and D enables according to the invention the calculation of factor 'L', herein defined as: L=S/D. It was found, surprisingly, that if factor L is kept within certain limits, an inulin product is obtained that has a reduced tendency, or even no tendency at all, to gel formation in aqueous systems; at the same time, the inulin product shows may characteristics for which inulin is known, such as prebiotic properties and texture-giving properties. Thus, according to the invention, factor L should have a value in the range from 2.0 until and including 3.0.

The inulin product of the invention contains at least 3 wt. % (measured on total carbohydrates) of inulin compounds of formula $GF_n$ wherein n is 10 or greater and/or of formula $F_m$ wherein m is 11 or greater. This has the advantage that the product can exhibit typical properties that are associated with inulin compounds of somewhat higher DP. Preferably, the inulin product of the invention contains at least 5, 6, 7, 8, 9 or at least 10 wt. % (measured on total carbohydrates) of inulin compounds of formula $GF_n$ wherein n is 10 or greater and/or of formula $F_m$ wherein m is 11 or greater.

The inulin product of the invention contains at most 20 wt. % (measured on total carbohydrates) of inulin compounds of formula $GF_n$ wherein n is 10 or greater and/or of formula $F_m$ wherein m is 11 or greater. This has the advantage that a balance is struck between properties as conferred by inulin compounds of somewhat higher DP and inulin compounds of DP's of up to 10. Preferably, the inulin product of the invention contains at most 18, 16, 14, 12, or at most 11 wt. % (measured on total carbohydrates) of inulin compounds of formula $GF_n$ wherein n is 10 or greater and/or of formula $F_m$ wherein m is 11 or greater.

As is known, inulin products can—and often do—in practice contain some amount of non-inulin compounds, including non-inulin carbohydrates. Typical examples of non-inulin carbohydrates are free glucose, free fructose, and sucrose. The inulin product according to the invention preferably contains at most 30 wt. % (as measured on total carbohydrates) of non-inulin carbohydrates. More preferably, the inulin product of the invention contains between 0.5 or 1 and 30, preferably at most 25, 20, 15, or even at most 12, 10, 8, 6, 5, or 4 wt. % (as measured on total carbohydrates) of non-inulin carbohydrates.

In a preferred embodiment of the inulin product of the invention, the value of factor L is at least 2.05, more preferably at least 2.10, 2.15, 2.20, 2.25, 2.30, 2.35, 2.40, 2.45, or even at least 2.50. Preferably, the value of factor L is at most 2.95, 2.90, 2.85, 2.80, 2.75, 2.70, 2.65, or even 2.60.

The inulin compounds in the inulin product of the invention can be of any suitable source or combination of sources; in a preferred embodiment, the inulin compounds are for at least 40 wt % originating from chicory roots; more preferably the inulin compounds are for at least 50, 60, 70, 80, 90, or even for essentially 100 wt. % originating from chicory. Preferably, the inulin compounds are for 100% originating from chicory.

As used herein, the terms 'essentially', 'consist(ing) essentially of', 'essentially all' and equivalents have, unless noted otherwise, in relation to a composition or a process step the usual meaning that deviations in the composition or process step may occur, but only to such an extent that the essential characteristics and effects of the composition or process step are not materially affected by such deviations.

As noted above, it is an advantage of the inulin product of the invention that its tendency to form gels is greatly reduced or even absent. A preferred embodiment of the invention, therefore, relates to an aqueous dispersion or solution of the inulin product of the invention. The specific advantages of the invention are especially then visible if the said aqueous dispersion or solution contains between 45 and 80, preferably at least 50, 55, 60, 65, 70, or even at least 71, 72, 73, 74, or 75 wt. % of the inulin product of the invention.

The invention further relates to a food product or pet food product or animal feed that contains an inulin product according to the invention or an aqueous dispersion or solution thereof.

In a main embodiment, the invention relates to a favourable method of preparing the inulin product of the invention. This method comprises:

a preparatory step, wherein an inulin raw material is brought into aqueous solution to form an inulin solution, whereby the inulin raw material has a value of factor L below 2.0 and whereby the inulin raw material contains between 8 and 75 wt. % of $GF_n$ compounds wherein n is 10 or greater and/or $F_m$ compounds wherein m is 11 or greater; and a conversion step, wherein a hydrolysis of the inulin raw material in the inulin solution is executed, such that the inulin product of the invention is formed.

In the preparatory step of the method of the invention, an inulin raw material is used. The inulin raw material can be of any suitable source, provided that it has a value of L below 2.0. Preferably, the value of L of the inulin raw material lies between 0.25 and 0.75. Furthermore, the inulin raw material should contain a sufficient amount of between 8 and 75 wt. %, preferably at least 10, 15, 20, 25, 30, 35, 40, 45, or even at least 50 wt. %, of $GF_n$ compounds wherein n is 10 or greater and/or $F_m$ compounds wherein m is 11 or greater in order to ensure that during the conversion step, to be discussed below, the inulin product of the invention can be formed.

Preferably, the inulin raw material originates from chicory roots. Such inulin raw materials are as such known. Native inulin from chicory roots, i.e. inulin that has only been subjected to the steps necessary to isolate it from the roots but not to further steps that modify its nature and also referred to as native chicory inulin, is an example of a suitable inulin raw material.

The inulin raw material is brought into aqueous solution. For many inulin raw materials, this will entail raising the temperature to above room temperature—to for example between 50 and 110° C. preferably to at least 60, 70, 80, or even to 90 or 95° C.—in order to ensure that also the longer-chain inulin compounds are dissolved, to form an inulin solution. Preferably, the inulin solution contains between 20 and 50 wt. % of the inulin raw material.

Following the preparatory step, the inulin solution is subjected to a conversion step. In the conversion step, a hydrolysis of the inulin raw material in the inulin solution is executed. Such a hydrolysis is as such known, and can be done via chemical routes—e.g., by reducing the pH—or by subjecting the inulin solution to the action of an enzyme. The hydrolysis must be done in such a way that the value of factor L raises from below 2.0 to within the range of values or preferred values of factor L of the inulin product of the invention as discussed above. In other words, the hydrolysis step must cause the formation of a sufficient amount of compounds that constitute factor S, i.e. $GF_2$, $F_3$, and $F_4$; this will lead to an increase of the value of the S and consequently to an increase of the value of factor L. In the case of the execution of the conversion step by means of an enzymatic hydrolysis, enzymes that act primarily by removing one fructose moiety from the end tail of an inulin compound—a mode of action often found among exoinulinases—are typically less suitable for the method of the invention. By contrast, it was found that endo-inulinases such as in particular those classified in EC 3.2.1.7 are often quite suitable for use in the conversion step of the invention.

It is noted that the required intensity of the hydrolysis in the conversion step is different, namely lower, compared to a hydrolysis that has as target to prepare an oligofructose from an inulin raw material. Consequently, the precise conditions of the conversion step will be different from a method of preparing oligofructose from an inulin raw material. For an enzymatic conversion, the differences will typically lie in a combination of a different enzyme concentration—which may be lower for the method of the invention compared to an oligofructose-preparing process—with process parameters like solids content, temperature, pH, and/or duration. It may thus be that some routine experimentation is needed to find a suitable type and amount of enzyme and to find suitable values of temperature, pH, or concentrations in order to execute the conversion step of the invention; this applies mutatis mutandis also in case the conversion step is executed by means of acidic hydrolysis.

The invention furthermore relates to a process for the preparation of an inulin composition, comprising:
an initial step, wherein an inulin raw material is brought into aqueous solution to form an inulin solution, said inulin raw material having a value of L below 2.0 and being a native chicory inulin;
a reaction step, wherein a hydrolysis of the inulin raw material in the inulin solution is executed such that the value of L lies between 2.0 and 3.0, to form the inulin composition.

The initial step in the process to prepare an inulin composition is the same as the preparatory step described above in relation to the preparation of the inulin product of the invention, including any embodiments of the preparatory step, with however the boundary condition that the raw material should be a native chicory inulin, i.e. a native inulin from chicory roots. The reaction step in the process to prepare an inulin composition is the same as the conversion step described above in relation to the preparation of the inulin product of the invention, including any embodiments of the conversion step.

The invention will be illustrated by the following Example and Comparative Evaluation, without being limited thereto.

Example

Native inulin from chicory root was used as the inulin raw material. The value of factor L was determined according to the methods described above and was found to be 0.40. The weight percentage (on total carbohydrates) of compounds $GF_n$ and/or $F_m$ having a DP of 11 or higher was determined to be 50.6 wt. %.

The preparatory step of the invention was done by making a 28 wt. % aqueous solution of the inulin raw material at 64° C. The conversion step according to the invention was done in a batch reactor via enzymatic hydrolysis with a low dosage of 0.15 U/gram dry matter of Novozymes 960 (non-immobilized) as enzyme at 64° C. during 20 hours at pH 5.1. The hydrolysis was halted by bringing the pH to 6.5.

The resulting product was analysed using HGC according to the method as referred to above. Factor S was determined to be 25.4 wt. %; factor D was determined to be 10.8; consequently, factor L was calculated to be 2.35. The weight percentage (on total carbohydrates) of compounds of $GF_n$ and/or $F_m$ having a DP of 11 or higher was determined to be 15.9 wt. %. The non-inulin carbohydrates in the inulin product were free glucose, free fructose and sucrose, in a combined amount of 9.7 wt %.

The aqueous solution of the inulin product was concentrated via evaporation to a solids content of 70 wt. %, which step also caused the enzyme to be permanently deactivated, then left undisturbed and allowed to cool to room temperature. No gel-forming was observed: not initially, nor after cooling down to room temperature.

Comparative Evaluation

An evaluation was made of example 1 of US-A-2001/016572. The evaluation yielded the following information:
Table 1 of US-A-2001/016572 details, under the heading 'The composition of the invention . . . ' the composition of an inulin product.
The inulin product contains 0.18 wt. % $GF_2$, 32 wt. % $F_3$, and 31.11 wt. % $F_4$. It follows that the value of parameter S is 63.29.
The inulin product was not prepared from native inulin, but rather from a raw material consisting of inulin having an average degree of polymerisation (DP) of 27, without any GF, free F, or free G. From this, it follows that parameter D has a value of 27.
Factor L is 63.29/27 which equals 2.34
The inulin product does not contain any GFn compounds in which n is 10 or greater, nor any Fm compounds in which m is 11 or greater.

The inulin product of the Comparative Evaluation did not provide any significant texturizing properties to food products such as yoghurts or fruit preparations, in contrast to the inulin product of the Example according to the invention, which did provide such texturizing properties.

The invention claimed is:

1. A polydisperse inulin product having a factor L, defined as a ratio S/D, wherein:
S equals a sum of the compounds $GF_2$, $F_3$, and $F_4$ in the inulin product, expressed in wt. % on total carbohydrates;
D equals $[(F_i/G_i)+1]$, wherein $F_i$ is an amount of inulin-related fructose in the inulin product, $G_i$ is an amount of inulin-related glucose in the inulin product, whereby $F_i$ and $G_i$ are expressed in wt. % on total carbohydrates,
wherein the value of L lies between 2.2 and 3.0, and wherein between 3 and 20 wt. % of total carbohydrates of the inulin product comprises:
$GF_n$ compounds wherein n is 10 or greater, and/or
$F_m$ compounds wherein m is 11 or greater.

2. The inulin product according to claim 1, wherein the inulin product contains at most 30 wt. % of total carbohydrates of non-inulin carbohydrates.

3. The inulin product according to claim 1, wherein the value of L lies between 2.2 and 2.8.

4. The inulin product according to claim 1, wherein the inulin product is derived from native chicory inulin.

5. An aqueous dispersion or aqueous solution, comprising the inulin product of claim 1, dispersed or dissolved in water or an aqueous phase.

6. A food product or animal feed or pet food product, containing an inulin product as claimed in claim 1.

7. A food product or animal feed or pet food product, containing an aqueous dispersion or an aqueous solution of an inulin product as claimed in claim 5.

8. A process for the preparation of an inulin product as claimed in claim 1, comprising the steps of:
a preparatory step, wherein an inulin raw material is brought into aqueous solution to form an inulin solution, wherein the inulin raw material has a value of factor L below 2.0 and contains between 8 and 75 wt. % of $GF_n$ compounds wherein n is 10 or greater and/or $F_m$ compounds wherein m is 11 or greater; and a conversion step, wherein a hydrolysis of the inulin raw material in the inulin solution is executed, such that the inulin product having a value of L lying between 2.2 and 3.0 is formed.

9. The process according to claim 8, wherein the inulin raw material is a native chicory inulin.

10. The process according to claim 9, wherein the native chicory inulin has a value of L lying between 0.25 and 0.75.

11. The inulin product according to claim 2, wherein the non-inulin carbohydrates are selected from the group consisting of free glucose, free fructose and sucrose.

12. The inulin product according to claim 2, wherein the value of L lies between 2.2 and 2.8.

13. The inulin product according to claim 2, wherein the inulin product is derived from native chicory inulin.

14. The inulin product according to claim 3, wherein the inulin product is derived from native chicory inulin.

15. An aqueous dispersion or aqueous solution, comprising the inulin product of claim 2, dispersed or dissolved in water or an aqueous phase.

16. An aqueous dispersion or aqueous solution, comprising the inulin product of claim 3, dispersed or dissolved in water or an aqueous phase.

17. An aqueous dispersion or aqueous solution, comprising the inulin product of claim 4, dispersed or dissolved in water or an aqueous phase.

18. An aqueous dispersion or aqueous solution, comprising the inulin product of claim 11, dispersed or dissolved in water or an aqueous phase.

\* \* \* \* \*